US010674993B2

(12) United States Patent
Wei et al.

(10) Patent No.: US 10,674,993 B2
(45) Date of Patent: Jun. 9, 2020

(54) ANALYSIS OF MITRAL REGURGITATION BY ULTRASONIC IMAGING

(75) Inventors: Qifeng Wei, Wayland, MA (US); Karl Thiele, Andover, MA (US); Ajit Yoganathan, Tucker, GA (US); Choon-Hwai Yap, Pittsburgh, PA (US)

(73) Assignees: KONINKLIJKE PHILIPS N.V., Eindhoven (NL); GEORGIA TECH RESEARCH, Atlanta, GA (US)

( * ) Notice: Subject to any disclaimer, the term of this patent is extended or adjusted under 35 U.S.C. 154(b) by 1079 days.

(21) Appl. No.: 13/994,794

(22) PCT Filed: Dec. 16, 2011

(86) PCT No.: PCT/IB2011/055739
§ 371 (c)(1),
(2), (4) Date: Jun. 17, 2013

(87) PCT Pub. No.: WO2012/085797
PCT Pub. Date: Jun. 28, 2012

(65) Prior Publication Data
US 2013/0274606 A1 Oct. 17, 2013

Related U.S. Application Data

(60) Provisional application No. 61/426,669, filed on Dec. 23, 2010, provisional application No. 61/466,046, filed on Mar. 22, 2011.

(51) Int. Cl.
*A61B 8/06* (2006.01)
*G01S 15/89* (2006.01)
(Continued)

(52) U.S. Cl.
CPC ............. *A61B 8/06* (2013.01); *A61B 8/0883* (2013.01); *A61B 8/13* (2013.01); *A61B 8/488* (2013.01);
(Continued)

(58) Field of Classification Search
CPC ....... A61B 8/463; A61B 8/488; A61B 8/4444; A61B 8/5223; A61B 8/145; A61B 8/5207; A61B 8/4488
(Continued)

(56) References Cited

U.S. PATENT DOCUMENTS

| | | |
|---|---|---|
| 4,913,159 A | 4/1990 | Gardin et al. |
| 5,606,972 A | 3/1997 | Routh |

(Continued)

OTHER PUBLICATIONS

Vandervoort, P.M., et al., Automated flow rate calculations based on digital analysis of flow convergence proximal to regurgitant orifices. Journal of the American College of Cardiology, 1993.22(2): p. 535-41.*

(Continued)

*Primary Examiner* — Jeffrey G Hoekstra
*Assistant Examiner* — Katherine M McDonald

(57) ABSTRACT

An ultrasonic diagnostic imaging system is described which quantifies regurgitant flow through a mitral valve. A flow quantification processor (34) in the ultrasound system produces a mathematical model of a flow velocity field proximal to a regurgitant orifice. The velocity field model produces values of velocity vectors directed toward the regurgitant orifice. These modeled values are modified for the effects of ultrasound physics and ultrasound system operation to produce expected velocity values. The expected velocity values are compared with actual Doppler velocities measured by the ultrasound system, and the differences accumulated to a mean square error which is used to adjust parameters of the model such as the orifice location and flow velocities. When this iterative processing converges with a desired comparison, parameters derived from the finally adjusted model are used to calculate the true orifice location, flow rate, and volume flow.

17 Claims, 4 Drawing Sheets

(51) Int. Cl.
*A61B 8/13* (2006.01)
*A61B 8/08* (2006.01)

(52) U.S. Cl.
CPC ....... *G01S 15/8979* (2013.01); *G01S 15/8993* (2013.01)

(58) Field of Classification Search
USPC ........................................ 600/456, 454, 441
See application file for complete search history.

(56) References Cited

U.S. PATENT DOCUMENTS

| | | | |
|---|---|---|---|
| 5,997,479 | A | 12/1999 | Savord et al. |
| 6,013,032 | A | 1/2000 | Savord |
| 6,283,919 | B1 | 9/2001 | Roundhill et al. |
| 6,443,896 | B1 | 9/2002 | Detmer |
| 6,458,083 | B1 | 10/2002 | Jago et al. |
| 6,468,216 | B1 | 10/2002 | Powers et al. |
| 6,530,885 | B1 | 3/2003 | Entrekin et al. |
| 6,623,432 | B2 | 9/2003 | Powers et al. |
| 6,719,697 | B2 | 4/2004 | Li |
| 8,911,375 | B2 | 12/2014 | Schreckenberg et al. |
| 2002/0151794 | A1 | 10/2002 | Li |
| 2011/0196237 | A1* | 8/2011 | Pelissier ................ A61B 8/06 600/454 |

OTHER PUBLICATIONS

Buck, Thomas, et al., Broad-Beam Spectral Doppler Sonification of the Vena Contracta Using Matrix-Array Technology. 2005, Journal of the American College of Cardiology, vol. 45, No. 5, pp. 770-779.*

Miyatake, Kunio, et al., Semiquantitative Grading of Severity of Mitral Regirgitation by Real-Time Two-Dimensional Doppler Flow Imaging Technique. 1986, Journal of the American College of Cardiology, vol. 7, No. 1, pp. 82-88.*

Vandervoort, P.M., et al., Application of Color Doppler Flow Mapping to Calculate Effective Regurgitant Orifice Area. Circulation, vol. 88, No. 3, 1993: pp. 1150-1156.*

Cannon et al: "Measurement of Valvular Regurgitant Volume by Gain-Corrected Doppler in a Pulsatile Flow Model": Proceedings of the Annual International Conference of the IEEE Engineering in Medicine and Biology Society, 1988, p. 231.

* cited by examiner

ANALYSIS OF MITRAL REGURGITATION BY ULTRASONIC IMAGING

This application claims the benefit of U.S. provisional patent application Ser. No. 61/426,669, filed Dec. 23, 2010.

This invention relates to medical diagnostic ultrasound systems and, in particular, to the use of diagnostic ultrasonic imaging systems for the analysis of mitral regurgitation flow.

Regurgitant flow is a serious medical condition which required analysis and appropriate treatment. Just prior to the contraction of the left ventricle to pump blood into the body, the mitral valve must close completely so that the contraction will eject all of the blood flow into the aorta. If the valve does not close completely, some of the blood in the left ventricle will be ejected back into the left atria through the opening in the incompletely sealed valve. This backflow of blood, typically a small, momentary jet of blood flow squirting back through the incompletely closed valve leaflets, reduces the outflow of blood from the heart and hence the efficiency of each heart contraction. The heart must then pump more rapidly in order to supply the body with its necessary supply of nourishing blood flow. The heart is overworked due to its inefficiency, leading to heart failure.

Clinicians have used ultrasonic imaging for many years to try to detect regurgitant blood flow. Ultrasonic detection of valvular regurgitation was initially done by looking for the above-mentioned jet of blood in an ultrasound image of the left side of the heart. During the past twenty years observation of the jet has been facilitated by two dimensional (2D) colorflow Doppler imaging, in which the high speed and turbulence of the small jet of blood is detected by careful search for these abnormal local flow velocities near the leaking heart valve. But acquisition of the image plane in which the jet is most prevalent, coupled with heart and valve motion and blood flow turbulence in the vicinity of the mitral valve, as well as the momentary occurrence of the jet, pose challenges to this subjective approach. In recent years, in cases where the location of the jet can be observed ultrasonically, clinicians have used a technique called PISA, an acronym for Proximal Iso-velocity Surface Area, to try to quantify the regurgitant blood flow. In this method the suspect valve and the region inside the LV heart chamber and proximal to the valve are imaged by colorflow Doppler imaging. At the time of occurrence of the jet a flow convergence region (FCR) is formed in the proximal region as blood flow velocities in the region instantaneously accelerate toward the regurgitant orifice. This flow pattern results in aliasing in the colorflow image as the flow velocities momentarily exceed the velocity range used for the colorflow image. A colorflow image at this moment is captured and frozen on the display screen. A measurement is then made of the velocity v at the first aliasing line of the FCR, and a measurement is made of the distance r from the aliasing line to the presumed center of the valve orifice. These two measurements are then used to compute the flow rate through the orifice using the expression $Q_r=2\pi r^2 v$.

Several difficulties arise when conducting this procedure. One is that the greatest accuracy is obtained when the jet is captured in the colorflow image at its very peak. The duration of the jet during a heart cycle can be only 300-450 milliseconds, however, while a typical colorflow frame rate may be in the range of 10-20 frames per second. Thus it is probable that the time of acquisition of one of the colorflow image frames will not be the same as the exact moment when the jet is at its peak. The clinician can repeat the colorflow acquisition sequence for additional cardiac cycles, or can settle for the inaccuracy causes by making the measurements at other than the exact peak of the jet.

Another problem is that the center of the valve orifice is not easy to define in the colorflow image. The valve tissue produces large reflections of ultrasound and is moving rapidly as scanning takes place, and can appear as a bulky, blurred or indistinct mass in the image. Thus it is possible that the accuracy of the measurement r will be compromised by the inability to estimate the exact location of the orifice.

Yet a third problem is that the basic PISA technique is only a single, one-dimensional measurement. Only one velocity measurement is made and only a single radius r to the orifice is used in the computation. The method assumes that the rest of the blood flow in the FCR is behaving the same as that of the single measurement. Obviously, any inaccuracy in making the single measurement will yield an inaccurate result.

An extension of the basic PISA technique which attempts to cure these inaccuracies is to make multiple velocity measurements around the arc delineating the outer boundary of the FCR in the two dimensional image. The distance r from each velocity measurement point to the orifice is measured, and the multiple measurements are used to calculate the flow rate $Q_r$. While the multiple measurements may prevent reliance on a single inaccurate measurement, another problem arises. The single measurement (1D) technique generally is done by aiming a center beam of the ultrasound probe through the apex of the heart and directly through the presumed regurgitant orifice, and making the velocity v and distance r measurements along this beam line. With the beam line thus aligned with this vector of the regurgitant flow, the velocity measured will be accurate and not affected by a non-zero Doppler angle. As is well known, ultrasound Doppler velocity measurements are affected by the angle between the flow direction and the ultrasound beam direction. Flow which is directly in line with the beam direction will be accurately measured, whereas flow which is at a non-zero angle to the beam direction will be reduced by the cosine of the angle. Flow which is orthogonal (90°) to the beam direction will produce no Doppler response. Hence, a Doppler velocity measured by ultrasound must be corrected as a function of the angle between the flow vector and the beam direction in order to produce a more accurate velocity measurement. In the case of the 2D PISA technique, the additional velocity measurements along the FCR arc will be inaccurate due to variation of the angles between their flow vectors and the beam direction at each point where a velocity measurement is made. Thus, whereas multiple measurements can compensate for an error made in a single velocity measurement, the aggregate measurements will understate the flow rate due to the variation in the Doppler angles at each measurement point.

Yet a further problem inherent in the PISA technique is inaccuracy in knowing the precise location of the regurgitant orifice of the valve. As mentioned above, aliasing in the colorflow image is prevalent in the vicinity of the valve leak due to the sudden acceleration of the blood flow toward and through the orifice. The colorflow image is thus cluttered with the flash of aliasing colors in the Doppler image in the vicinity of the orifice. Additionally, the mitral valve plane is in motion during the heart contraction. As the accuracy of the PISA technique is reliant upon knowing the orifice location in order to measure the distance r, these impediments to precisely knowing the orifice location can result in an inaccurate r measurement and hence an inaccurate calculation of flow rate. Experiments have demonstrated that an error of as little as one millimeter in the orifice location can lead to a significant error in calculating the flow rate through the leak. Furthermore, it is known that many regurgitant valves do not have a single pinhole leak, but leak along a slit of imprecise valve closure. The assumption of a leak as being caused by a single pinhole through the valve may thus not be valid.

Accordingly it is desirable to provide a method and apparatus for quantifying the flow rate and volume flow of mitral valve regurgitation which overcomes the above limitations of the PISA technique. It is an object of the present invention to accurately identify the precise location of the orifice of the valve regurgitation. It is a further object of the present invention to make a range of measurements which are unaffected by the Doppler angle at each measurement location. It is a further object of the present invention to be able to identify and quantify mitral valve regurgitation due not only to a single pinhole leak, but also due to a slit along the closure of the valve.

In accordance with the principles of the present invention, an ultrasonic diagnostic imaging system and method are described for quantifying regurgitant blood flow. An arcuate (two dimensional) or hemispherical (three dimensional) region of blood flow is delineated proximal to a presumed location of a mitral valve leak in an ultrasound image of the regurgitant valve. The inner boundary of the region is at or just beyond the aliasing region adjacent to the orifice of the leak, and the outer boundary of the region is outward from and concentric with the inner boundary. Initial assumptions are made as to the regurgitant flow, including the location of the regurgitant orifice. These assumptions are used to compute a model of the velocity field of the regurgitant flow. The parameters of the model are adjusted in accordance with the physics of ultrasound and/or settings of the ultrasound system to determine expected velocity vectors to be observed by the ultrasound system, $V_{OBS}$ in the delineated region. Velocity measurements are made by the ultrasound system within the delineated region, and the measured velocities are compared with the expected velocities. Differences between the measured and expected values are computed and, through non-linear curve-fitting, adjustments are made to one or more of the model values. The processed is iteratively repeated until the expected and measured values acceptably converge. The iteratively adjusted model parameters can be used to produce a quantified measurement of the flow rate or the location of the leaking orifice in the valve.

In accordance with a further aspect of the present invention, an initially assumed location of the regurgitant orifice in the ultrasound image is automatically updated by the foregoing process to indicate the actual location of the orifice in the image. The clinician is thus shown a precise location of the regurgitant orifice despite the presence of image clutter in the vicinity of the mitral valve.

In accordance with yet another aspect of the present invention, the foregoing technique is repeated at multiple spatial locations along a mitral valve. The aggregate regurgitant flow measured at the spatial locations provides a measure of regurgitant flow due to a regurgitant leak which is a slit in the mitral valve closure rather than a single leaking pinhole orifice.

In accordance with a further aspect of the present invention, several wall filter characteristics are described which are preferred for an implementation of regurgitant flow measurement in accordance with the present invention, including a wall filter with a characteristic that peaks at intermediate flow velocities which are often found in a flow region proximal a regurgitant orifice.

Figure 1:
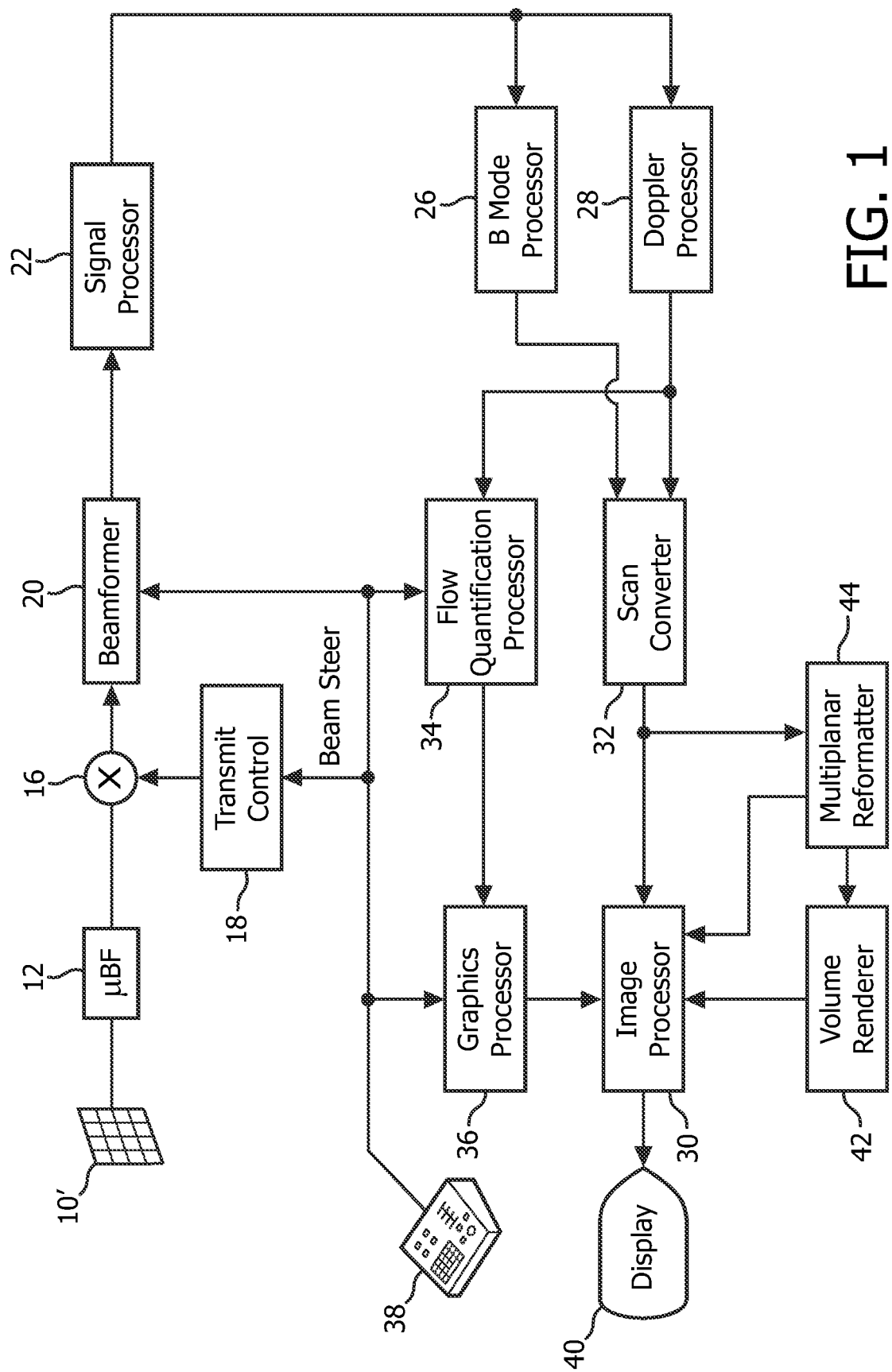
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. In FIG. 1 a transducer array 10' is provided in an ultrasound probe for transmitting ultrasonic waves and receiving echo information. The transducer array 10' is preferably a two dimensional array of transducer elements capable of scanning in three dimensions, for instance, in both elevation and azimuth about the location of the mitral valve, for 3D imaging. The transducer array is coupled to a microbeamformer 12 in the probe which controls transmission and reception of signals by the array elements. Microbeamformers are capable of at least partial beamforming of the signals received by groups or "patches" of transducer elements as described in U.S. Pat. No. 5,997,479 (Savord et al.), 6,013,032 (Savord), and 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 10 under control of the microbeamformer 12 is directed by the transmit controller 18 coupled to the T/R switch and the beamformer 20, which receives input from the user's operation of the user interface or control panel 38. One of the functions controlled by the transmit controller is the direction in which beams are steered. Beams may be steered straight ahead from (orthogonal to) the transducer array, or at different angles for a wider field of view.

The partially beamformed signals produced by the microbeamformer 12 are coupled to a main beamformer 20 where partially beamformed signals from the individual patches of elements are combined into a fully beamformed signal. For example, the main beamformer 20 may have 128 channels, each of which receives a partially beamformed signal from a patch of 12 transducer elements. In this way the signals received by over 1500 transducer elements of a two dimensional array can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle reduction, signal compounding, and noise elimination.

The processed signals are coupled to a B mode processor 26 and a Doppler processor 28. The B mode processor 26 employs amplitude detection for the imaging of structures in the body such as the tissue of the heart wall, the mitral valve, and blood cells. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor 28 processes temporally distinct signals from tissue and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. For mitral regurgitation assessment of a rapidly occurring jet, short ensemble lengths (fewer samples) are generally employed so that a high acquisition frame rate can be realized. The Doppler shift $\Delta f$ may be estimated by an equation of the form $$\Delta f = \frac{2 v f_0 \cos\theta}{c}$$

where $f_o$ is the transmit frequency, c is the ultrasound propagation speed, v is velocity, and θ is the angle between the beam direction and the direction of the blood flow.

The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40.

In accordance with the principles of the present invention, blood flow velocity values produced by the Doppler processor 28 are coupled to a flow quantification processor 34. The flow quantification processor operates as described below to produce a measure of the flow rate through a regurgitant orifice, the volume flow through the orifice, and the spatial location of the orifice. The flow quantification processor may receive input from the user control panel 38, such as an initial estimate of the location of the orifice as described below. Output data from the flow quantification processor is coupled to a graphics processor 36 for the reproduction of output data from the processor with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of a display of multiple multiplanar reformatted (MPR) images which may be used to quantify regurgitant flow in the MPR images in accordance with the present invention as described below.

Figure 2:
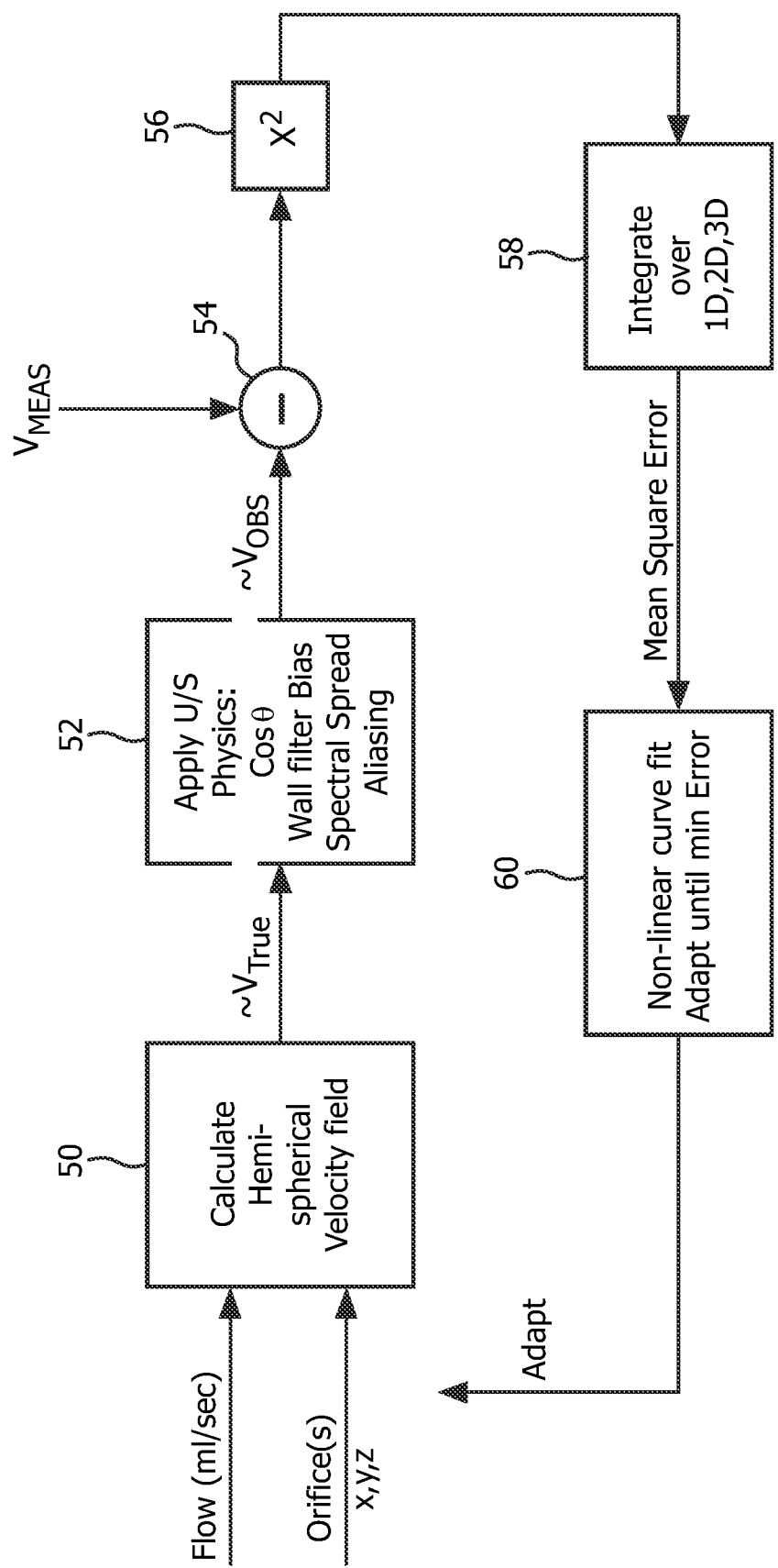
FIG. 2 is a block diagram illustrating the functioning of the flow quantification processor of FIG. 1.

FIG. 2 describes the operation of the flow quantification processor of FIG. 1. The processor is based upon a mathematical model of the flow velocity field at sample points within an inclusion zone as described below. In a 2D image embodiment the inclusion zone is preferably a curved strip delineated by two arcs centered on the regurgitant orifice location, $\{x_o, y_o, z_o\}$. In a 3D image embodiment the curved strip is of the form of a hemispherical shell, as discussed in conjunction with FIG. 3 below. In a preferred embodiment the model is a vector velocity model of the flow velocity field of the form $$\vec{V}_{Model}(r) = \vec{n}_{rel}|V(r)|$$

or $$\vec{V}_{Model}(r) = \frac{-\vec{r}}{\|\vec{r}\|}°|V(r)|$$

where $|V(r)|=\vec{F}/2\pi r^2$ for the flow vector $\vec{F}$, and r is the distance from a point at (x, y, z) in three dimensional coordinates in the inclusion zone to the regurgitant orifice, and the orifice is located at coordinates $\{x_o, y_o, z_o\}$ in three dimensional space. This means that the distance r, when expressed vectorially to indicate the direction to the orifice, is of the form $$r = \{x-x_o, y-y_o, z-z_o\}$$

In box 50 of FIG. 2, the flow velocity of every point in the inclusion zone is modeled in this way. Initially the model can start with assumed or estimated values for the unknown parameters, including the flow $\vec{F}$ and the $\{x_o, y_o, z_o\}$ location of the regurgitant orifice. For instance, the model can start with parameters which are nominally characteristic of regurgitant flow. The user can enter parameters such as by indicating the presumed location of the regurgitant orifice in the ultrasound image. Or a known technique such as PISA can be used to calculate values used as the starting parameters for the flow velocity field.

The flow velocity field model approximates velocity vectors which would be accurate if the true physiologic velocity vectors were known. The velocity vectors approximated by the model are indicated at the output of box 50 as $\sim V_{TRUE}$. Box 52 then imposes some limits and adjustments to $\sim V_{TRUE}$ due to practical factors such as the physics of ultrasound and operating parameters of the ultrasound system being used. The flow velocity field model is then adjusted or scaled to take these practical factors into account in consideration of the actual velocity values which would be observed by an ultrasound system. One of the practical factors for which adjustment can be made is the Doppler angle. As mentioned above, Doppler measurements as performed by an ultrasound system are precisely accurate only when the direction of flow is in line with the direction of the ultrasound beam, a Doppler angle of zero. For all other angles between the beam direction and the flow direction the velocity is understated. In the Doppler shift equation presented above, the Doppler angle is weighed in the result by the cos θ term, where θ is the Doppler angle. Another practical factor of an ultrasound system is wall filter bias. A Doppler wall filter will typically exhibit a nonlinear characteristic which, for blood flow detection, will have a zero response at DC (no motion) and rise to a maximum response at a selected high frequency of ±f. Alternatively, the wall filter can exhibit a maximum response at a frequency less than that dictated by the Nyquist limit of the ensemble sampling rate, as discussed below. A sample volume in the body at which the Doppler shift is measured will not be a single point in the body but will have a finite size, resulting in the return of Doppler signals indicative of a range of velocities. The non-uniform response of the wall filter can cause a wide spread of velocities to experience greater gain at different locations of the response characteristic, e.g., higher velocities are more greatly emphasized than lower velocities. This non-uniform response can produce a shift in the perceived center of the spread of velocities referred to as wall filter bias. The wall filter bias effect can also be taken into account by an adjustment to the model. Another related factor which can be taken into account is spectral spread, the Doppler spectral broadening effect resulting from the different paths and angles from the sample volume to each receiving element of the active aperture of an array transducer. See U.S. Pat. No. 5,606,972 (Routh). Yet another factor which can be taken into account is aliasing effects, the mis-reporting of Doppler frequencies and velocities when the motion of blood flow is at a velocity in excess of that which can be detected unambiguously by the Nyquist limit of the sampling rate of the echo ensemble. In box 52, factors such as these are taken into account by a dot product adjustment to the flow velocity field model which, for the models previous described, can be of the form $$\vec{V}_{OBS}(r) = |V(r)| \left[ \frac{-\vec{r}}{\|\vec{r}\|} \circ \vec{n}_{scan} \right]$$

where $\vec{n}_{scan}$ is a vectorial representation of the physical and ultrasound system factors for which adjustment is being made. The result as shown in FIG. 2 is $V_{OBS}$, the model as adjusted by expected effects and what is to be expected in the signals measured by the ultrasound system.

A comparator 54 compares the expected velocity values from the flow velocity field model, $V_{OBS}$, with actual velocity measurements from points (sample volumes) in the field, $V_{MEAS}$, produced by the Doppler processor 28. In box 56 the differences between the expected and received values are squared to produce an error term for each point. The error terms are integrated over the full inclusion zone which may be a one dimensional (e.g., 1D line), two dimensional (e.g., 2D line arcuate area), or three dimensional (e.g., 3D hemispherical shell) inclusion zone 58 to produce a mean squared error term form the full zone. The error term is then used to adjust the parameters of the field model such as r and the flow rate to cause a reduction in a subsequently measured error term. The preferred adjustment technique is to use a non-linear curve fit 60 to adapt the model toward error reduction. One such non-linear curve fitting technique which may be used is the Levengerg-Marquardt algorithm, which refines the coordinates of the regurgitant orifice location and the flow ($\vec{F}$) or flow rate ($Q_t$) of the field toward or through the orifice.

The loop of FIG. 2 is iteratively repeated to reduce the error term. With each pass through the loop a more precisely adapted field model is adjusted and compared with ultrasound velocity measurements from the acceptance zone and the error term is iteratively reduced. When the error term has been reduced to an acceptable low value, the model exhibits the desired actual measurements of the orifice location and the blood flow through the orifice. These terms, and others as desired, are produced as outputs by the flow quantification processor 34 and are presented on the display to the user.

Figure 3:
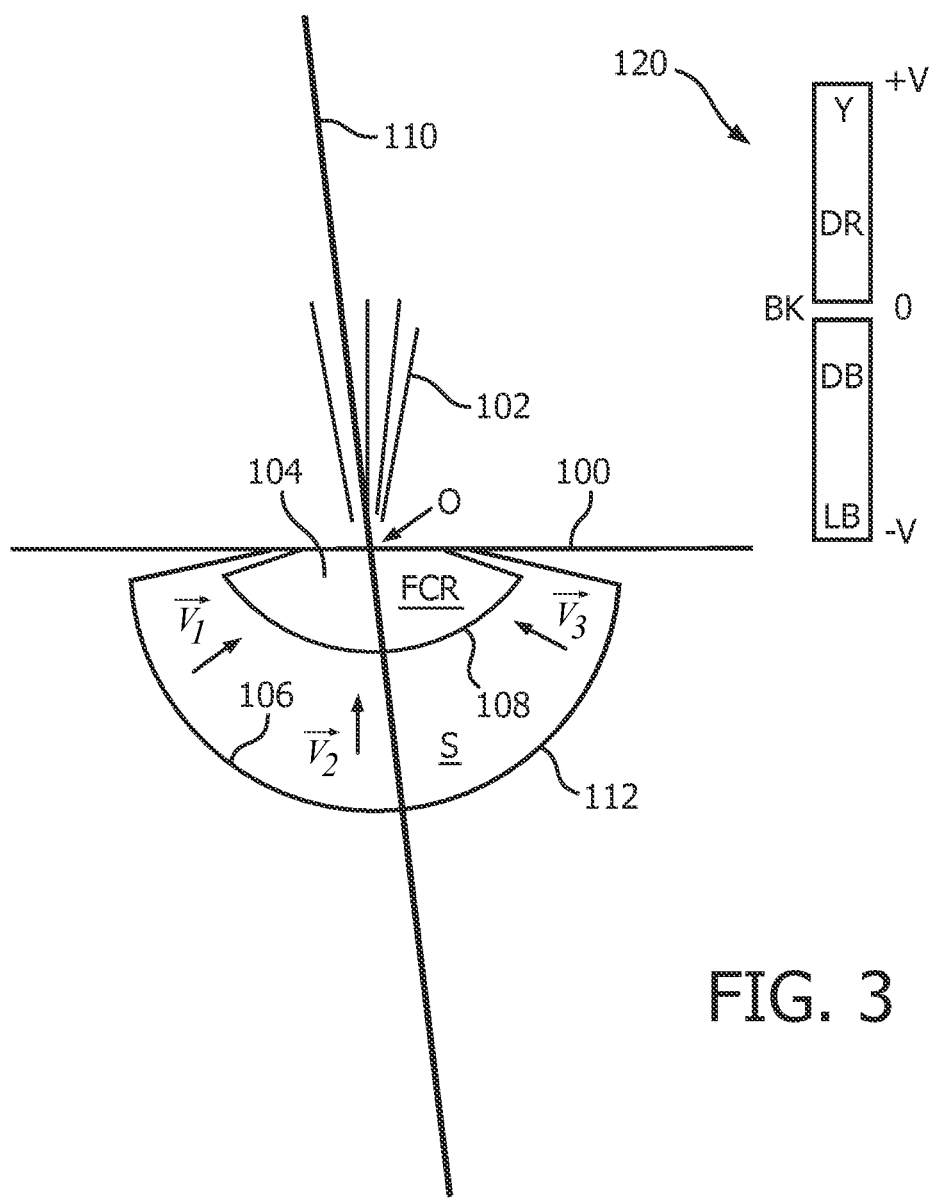
FIG. 3 illustrates an ultrasound Doppler image of a regurgitant jet.

FIG. 3 is a diagrammatic 2D ultrasound image illustrating practice of the present invention to measure mitral valve regurgitation. The line 100 represents the plane of the mitral valve on which a regurgitant leak exists through an orifice O. When the left ventricle contracts, a jet of blood 102 escapes back into the right atria. In the PISA method this jet would be interrogated by a Doppler beam 110 extending through the orifice O. U.S. Pat. No. 6,719,697 (Li) presents an improvement to the PISA technique in which a color M mode display is produced over the heart cycle from the location of Doppler beam 110. The color Doppler display processor is set for the display limits indicated by the color bar 120 on the right side of the image, extending from a zero velocity center reference (BK=black) to +V and −V maximum velocities in opposite directions. A range of colors (Y=yellow; DR-dark red; etc.) is displayed in accordance with this range of velocities. Aliasing occurs when a velocity being measured exceeds the Nyquist limits of +V and −V. Immediately adjacent the orifice is the flow convergent region (FCR) 104. Beyond the flow convergent region is the acceptance zone 112 (S) used by an implementation of the present invention.

Both the PISA technique and the present invention are premised on the assumption that the regurgitant flow in the left ventricle near the orifice is converging and flowing toward the orifice location O. This is indicated by the flow vectors $\vec{V}_1$, $\vec{V}_2$, and $\vec{V}_3$ in the acceptance zone S. But as the direction of the Doppler beam 110 illustrates, virtually all of the flow vectors will not be aligned with the beam direction, even when the varying beam angles of a phased array sector probe are used. Consequently there will be Doppler angles of different magnitudes for the different flow vectors, which is taken into account by the Doppler angle adjustments to the flow velocity field model in box 52 of FIG. 2 as described above.

The color Doppler image of the FCR 104 will be chaotic and erratic. This is because the spatial orientation of blood cells and blood flow velocities are changing very rapidly in this region as blood flow changes direction and accelerates momentarily toward the orifice O during systolic contraction. The ensemble samples acquired during this interval are often uncorrelated with one another, which defeats the correlation within an ensemble upon which the usual Doppler estimation processors are reliant. As a result, even thought the flow within the FCR may be generally laminar, the colorflow display can be that of highly turbulent flow and aliasing. The inner boundary 108 of the acceptance zone S is preferably set beyond the flow convergence region 104 to avoid the use of erratic velocity estimates from the FCR. One approach to setting the boundary 108 is to set it at or beyond the velocity shear boundary. This can be done visually with reference to the colorflow display, or automatically with reference to a velocity shear threshold.

The outer boundary 106 of the acceptance zone may be set in relation to measurable velocities. While the velocities of regurgitant flow are relatively high near the orifice, they become progressively lower at increasing distances from the orifice. The outer boundary 106 can be set at a distance from the orifice O at which low Doppler velocities can still be reliably measured. This may be determined in relation to a percentage of the Nyquist limit or in relation to a low flow velocity such as 5 mm/sec. The outer boundary 106 can thus be set at a distance at which acceptable sensitivity to low flows can still be realized by the Doppler processor.

The acceptance zone 112 in the example of FIG. 3 is seen to be a two dimensional arcuate area S having a center of rotation at the orifice O. The present invention may be used in one, two or three dimensions. A one dimensional implementation and model may just consider the segment of the beam line 110 which is between arcs 108 and 106, for instance. A two dimensional implementation would be one which samples an acceptance zone which is planar such as acceptance zone 112 in FIG. 3. A three dimensional implementation would consider an arcuate acceptance such as 112 but in a full hemisphere centered on the orifice. Greater accuracy would be anticipated with the two and three dimensional implementations. A preferred implementation would use a 3D imaging probe with a two dimensional array transducer as shown in FIG. 1, with acquisition and modeling done in a hemispherical or semi-hemispherical volume shell about the orifice. Higher frame rates can be realized with two dimensional imaging, in which case an MPR frame through the orifice and jet can be selected from the volume scanned with the 3D probe by use of the multiplanar reformatter 44. The desired plane can be repeatedly scanned at a high acquisition frame rate and the velocity measurements and flow calculations done with a two dimensional acceptance zone shown in the 2D MPR image.

While acceptance zones from which flow converges in a circular pattern toward the orifice can exist as shown in FIG. 3, other non-circular patterns have been found to be present in some cases. Stated differently, the flow vectors pointing toward the orifice may be arranged in a pattern other than an arc of a pure circle. Instead of the circular shape of FIG. 3, an acceptance zone may have a parabolic or flattened circular shape. In three dimensional implementations the acceptance zone may be a paraboloid or oblate spheroid shell. The shape of the acceptance zone, that is, the area or volume in which velocities are measured in comparison to the model, may be dynamically changed during iterative passages through the processing loop of FIG. 2 so that the process will adapt and converge to an acceptance zone with an altered shape from that used in the initial model.

Figure 4:
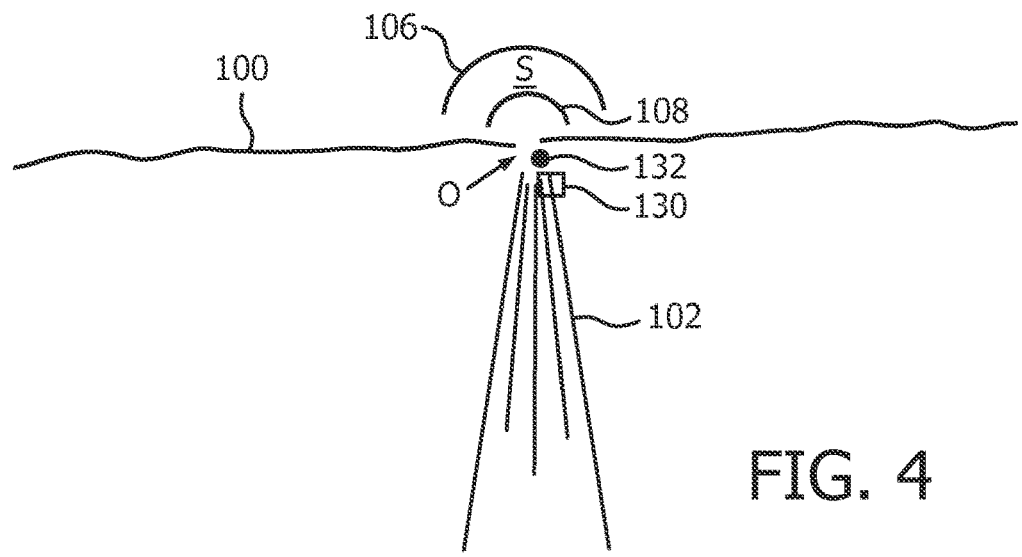
FIG. 4 illustrates an ultrasound image with an initially assumed orifice location and an automatically indicated orifice location in accordance with the present invention.

As previously mentioned, it is frequently difficult for a clinician to accurately pinpoint the location of a tiny regurgitant orifice on an ultrasound image. When the heart is not contracting, the orifice is not present, and when it is present, its location is marred by imaging artifacts of the resultant turbulence such as those in the vicinity of the flow convergence region. In accordance with a further aspect of the present invention, an implementation of the present invention can automatically indicate the location of a leaking orifice on an ultrasound image. FIG. 4 illustrates an ultrasound image in which elements previously described in conjunction with FIG. 3 bear the same reference numerals. This image also includes a small box 130 which has been placed over the image by a clinician at the start of a diagnosis to indicate the presumed location of the regurgitant orifice. A control of the control panel 38 such as the trackball is manipulated by the clinician to place the icon 130 at the location in the image where the clinician believes the orifice is located. The coordinates of the indicated orifice icon 130 are used to seed the processing of the flow quantification processor shown in FIG. 2, whereby the coordinates are used as the initial coordinates of the orifice in the mathematical model of box 50. The processor 34 iteratively refines the modeled values of the flow velocity vectors toward an orifice location in response to the receipt of the measured velocity values $V_{MEAS}$. The vertical placement of the orifice location has been found to have the greatest effect on the convergence of the modeled velocity vectors with the measured velocity values. While the heart is contracting during systole, the movement of contraction causes the mitral valve to move vertically in the image toward the center of the left ventricle. Thus, the natural contractive movement of the heart can be the source of greatest error in regurgitant flow assessment. The processor 34 iteratively refines the location of the orifice to reduce the error disparity between the measured and estimated velocity values in the flow velocity field (acceptance zone S) between boundaries 106 and 108. As the flow quantification processor iterates to converge on the true coordinates of the orifice, the finally determined coordinates are used by the flow quantification processor 34 and the graphics processor 36 to automatically move orifice icon 130 to the calculated coordinates in the image. Alternatively the graphics processor will place another (calculated) orifice icon 132 on the display at the true coordinate location determined by the iterative model adjustment. As mentioned previously, misplacement of the orifice by as little as 1 mm can significantly affect the orifice flow rate and volume flow calculations, volume flow being the integral of the flow rate over the time during which the heart is contract (about ⅓ of a heart cycle). The flow volume will peak at approximately the middle of the systolic interval. In FIG. 4 it is seen that the system has placed the calculated orifice icon 132 at its true location in the image field, which is different from the clinician's initial estimate of the orifice location. When the ultrasound study is performed with 2D imaging the orifice coordinates will generally be in (x,y,z) Cartesian coordinates. When 3D imaging is used a spherical $(r,\theta,\varphi)$ coordinate system will generally be employed. In addition, as the FIG. 4 ultrasound image illustrates, the acceptance zone S is graphically delineated in the displayed ultrasound image and any modification of the shape of the acceptance zone as discussed above is incorporated in the displayed shape and graphical delineation of the acceptance zone on the display.

Figure 5:
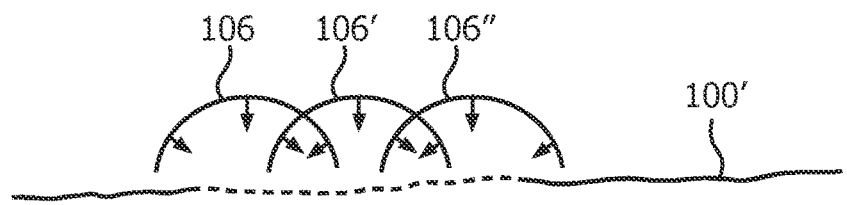
FIG. 5 illustrates a technique for quantifying the regurgitant flow of a slit along a valve in accordance with the present invention.

As mentioned above, regurgitant orifices do not always exist as single pinhole leaks in a closed valve. The leaks may be produced by slit openings or multiple small leaks. FIG. 5 is an illustration of the use of an implementation of the present invention to assess the flow rate and volume flow of slits and multiple leaks in valve closure. As FIG. 5 illustrates, the process of the present invention is performed for a series of orifice locations arrayed along the leaking mitral valve 100'. These discrete pinhole orifice locations can be used to model complex slit-like orifices or multiple orifices in the closed valve. FIG. 5 shows an example of three such determinations, each with its own acceptance zone, indicated by outer zone boundaries 106, 106' and 106'', and flow vectors (indicated by the small arrows) directed to converge at a different orifice location along the valve 100'. The vector velocity field associated with each pinhole orifice is combined vectorially with the other orifices, such that a single combined acceptance zone is defined along with a single combined vector velocity field.

For multiple orifices, the combined vector velocity field now approximates the true physiologic velocity vectors (~Vtrue, output of box 50 in FIG. 2). The processing of the combined vector velocity field determines the flow rate or volume flow of all the pinhole orifices corresponding to the entire slit along the mitral valve closure. While FIG. 5 gives an example of a vector velocity field generated from three pinhole orifices, any number of orifices may be used to adequately model the slit. The acceptance zones used for each measurement may be combined as shown in FIG. 5, as the flow that is determined for the combined orifices is vectorial flow directed toward a unique orifice or position along a slit. In a three dimension implementation the line of measurements is not constrained to a straight line in a plane, but may follow a non-linear path of closure of the mitral valve leaflets.

Figure 6:
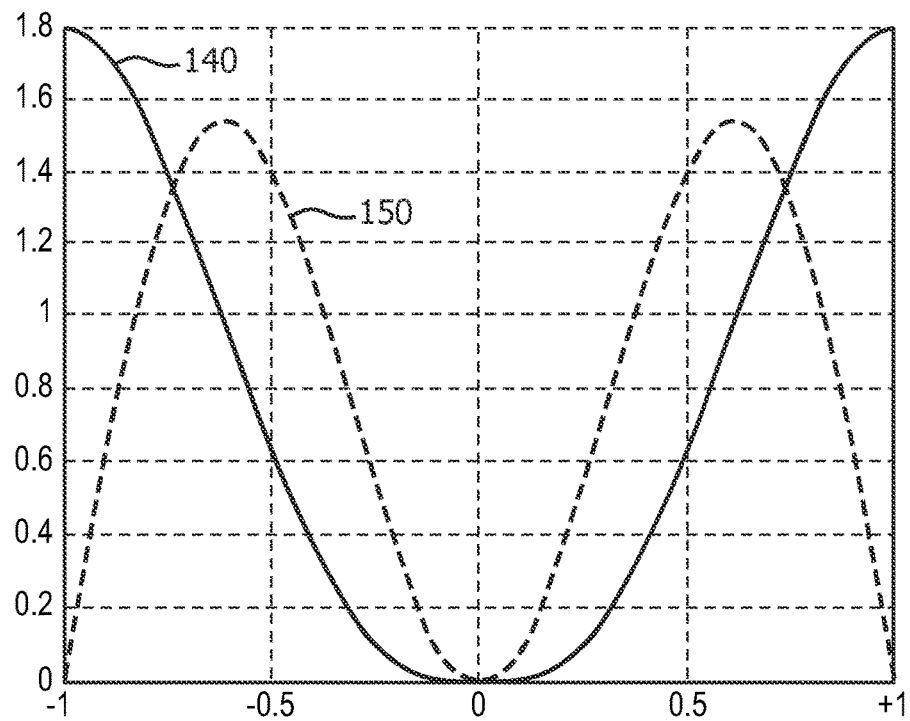
FIG. 6 illustrates the response characteristic of a wall filter suitable for use in an ultrasound system of the present invention.

FIG. 6 illustrates the response characteristics of two Doppler wall filters which may be employed in an implementation of the present invention. The coordinates of the abscissa of the plot of FIG. 6 are in units of the Nyquist limits of a sampled data wall filter, where the limits of +1 and −1 are the normalized Nyquist limits of the filter corresponding to the blood flow velocities. A zero (DC, or no-flow) condition is in the center. The ordinate coordinates indicate the relative amplitude response of the filter characteristic. The response curve 140 is a typical wall filter response curve for measuring blood flow and may be used in an implementation of the present invention. This characteristic has a response of zero at the center, resulting in no response to stationary objects such as stationary vessel walls. The response is seen to progressively increase as the curve extends out from zero, with a maximum response at the Nyquist limits for the highest velocity flows detectable without aliasing at the chosen sampling interval. As a result, this response characteristic is most sensitive to flow at the highest flow velocities.

The response curve 150 is one which is often preferred for the wall filter of an implementation of the present invention. The response of this curve 150 is seen to peak at a relatively high but intermediate sampling rate just above ±0.5 Nyquist, preferably in the range of ½ to ⅔ of Nyquist, and drops to a response of zero at the Nyquist limits. This filter characteristic is designed to be more sensitive to lower flow velocities, which can be expected around the outer boundary 106 of the acceptance zone S. This is helpful to offset the low sensitivity to low velocity flow which results from the short ensembles typically used for colorflow imaging of regurgitant flow. This can be seen by the greater response of the curve 150 for lower velocities near the center of the plot. While the curve 150 is seen to drop to zero at the Nyquist limits, this loss of high velocity sensitivity is generally acceptable when traded off for greater sensitivity to low velocity flows.

What is claimed is:

1. A diagnostic ultrasound system for measuring regurgitant flow comprising:
an ultrasound probe having a transducer array configured to transmit ultrasonic energy to and receive ultrasonic echoes from a location of regurgitant flow in a body;
an image processor configured to produce an ultrasound image of the location of regurgitant flow, based, at least in part, on received echoes;
a Doppler processor, configured to produce Doppler ultrasound measurements of blood flow velocity in the vicinity of the location of regurgitant flow, based, at least in part, on the received echoes;
a flow quantification processor configured to:
produce a model of a flow velocity field in the vicinity of the location of regurgitant flow, wherein the model derives approximated flow velocity values;
iteratively compare the approximated flow velocity values derived from the model with the flow velocity measurements produced by the Doppler processor;
calculate, at each iteration, error terms for all of the approximated flow velocity values based on the comparison of the approximated flow velocity values and the flow velocity measurements produced by the Doppler processor;
integrate the error terms over the flow velocity field to produce an integrated error term; and
iteratively adjust the model in response to the comparison, wherein an adjustment of the model reduces the integrated error term; and
a display device, coupled to the image processor and the flow quantification processor, the display configured to display the ultrasound image of the location of regurgitant flow and a flow measurement derived from the adjusted model of the flow velocity field.

2. The diagnostic ultrasound system of claim 1, wherein the flow quantification processor is further configured to adjust approximated flow velocity values for factors encountered when using an ultrasound system to measure velocity.

3. The diagnostic ultrasound system of claim 2, wherein the factors include at least one of effects due to the physics of ultrasound and operating parameters of the ultrasound system being used to measure velocity.

4. The diagnostic ultrasound system of claim 3, wherein one of the factors comprises the Doppler angle.

5. The diagnostic ultrasound system of claim 3, wherein one of the factors comprises wall filter bias.

6. The diagnostic ultrasound system of claim 3, wherein one of the factors comprises Doppler spectral broadening.

7. The diagnostic ultrasound system of claim 3, wherein one of the factors comprises aliasing effects.

8. The diagnostic ultrasound system of claim 1, wherein the flow velocity field comprises an acceptance zone in the vicinity of an orifice, the acceptance zone exhibiting a two dimensional arcuate shape.

9. The diagnostic ultrasound system of claim 1, wherein the flow velocity field comprises an acceptance zone in the vicinity of an orifice, the acceptance zone exhibiting a three dimensional hemispherical shape.

10. The diagnostic ultrasound system of claim 1, wherein the adjustment of the model comprises an adjustment to the approximated flow velocity values derived from the model.

11. The diagnostic ultrasound system of claim 1, wherein the adjustment of the model comprises an adjustment to the shape of the flow velocity field.

12. The diagnostic ultrasound system of claim 11, wherein the adjusted shape of the flow velocity field comprises one of a parabolic shape, a flattened circular shape, a paraboloid, or an oblate spheroid.

13. The diagnostic ultrasound system of claim 1, wherein the adjustment of the model comprises an adjustment to a location of or a distance to a regurgitant orifice.

14. A method for assessing regurgitant flow with an ultrasound system comprising:
   imaging with an ultrasound probe and an image processor a location of regurgitant flow in a body;
   producing a model of a flow velocity field in the vicinity of the location of regurgitant flow;
   producing Doppler ultrasound measurements of blood flow velocity in the vicinity of the location of regurgitant flow;
   comparing approximated flow velocity values derived from the model with the Doppler ultrasound measurements of blood flow velocity;
   calculating error terms for all of the approximately flow velocity values based on the comparison of the approximated flow velocity values and the Doppler ultrasound measurements of blood flow velocity;
   integrating the error terms over the flow velocity field to produce an integrated error term;
   adjusting one or more parameters of the model in response to the comparison, wherein an adjustment of one or more parameters reduces the integrated error term; and
   displaying an ultrasound image of the location of regurgitant flow and a flow measurement derived from a parameter of the adjusted model.

15. The method of claim 14, further comprising adjusting the model of the flow velocity field for an effect of one or more of the physics of ultrasound or an operating parameter of the ultrasound system prior to the comparing step.

16. The method of claim 14, wherein producing further comprises producing a model of an arcuate flow velocity field located in the vicinity of a regurgitant orifice.

17. The method of claim 14, wherein producing further comprises producing a model of a hemispherical flow velocity field located in the vicinity of a regurgitant orifice.

* * * * *